(12) United States Patent
Heo

(10) Patent No.: US 12,390,302 B2
(45) Date of Patent: Aug. 19, 2025

(54) DENTAL STENT

(71) Applicant: NEOBIOTECH CO., LTD., Gangwon-do (KR)

(72) Inventor: Chaeheon Heo, Seoul (KR)

(73) Assignee: NEOBIOTECH CO., LTD., Gangwon-do (KR)

( * ) Notice: Subject to any disclaimer, the term of this patent is extended or adjusted under 35 U.S.C. 154(b) by 393 days.

(21) Appl. No.: 17/969,112

(22) Filed: Oct. 19, 2022

(65) Prior Publication Data
US 2023/0380931 A1    Nov. 30, 2023

(30) Foreign Application Priority Data

May 27, 2022  (KR) .................. 10-2022-0065370

(51) Int. Cl.
| | |
|---|---|
| *A61C 1/08* | (2006.01) |
| *A61B 1/04* | (2006.01) |
| *A61B 1/24* | (2006.01) |
| *A61C 5/00* | (2017.01) |
| *A61C 5/80* | (2017.01) |
| *A61C 9/00* | (2006.01) |

(52) U.S. Cl.
CPC ............. *A61C 1/082* (2013.01); *A61B 1/04* (2013.01); *A61B 1/24* (2013.01); *A61C 5/007* (2013.01); *A61C 5/80* (2017.02); *A61C 9/0006* (2013.01)

(58) Field of Classification Search
CPC .................. A61C 5/80; A61C 5/007
See application file for complete search history.

(56) References Cited

U.S. PATENT DOCUMENTS

| | | | | |
|---|---|---|---|---|
| 185,665 | A * | 12/1876 | Brown .............. | A61C 5/82 433/161 |
| 421,952 | A * | 2/1890 | Marshall .......... | A61C 5/88 76/5.1 |
| 1,351,108 | A * | 8/1920 | Littlejohn ........ | A61C 9/0006 433/46 |
| 1,372,772 | A * | 3/1921 | Nishi .............. | A61C 5/77 433/223 |
| 1,402,298 | A * | 1/1922 | Kidder ............ | A61C 9/0006 433/46 |
| 1,422,488 | A * | 7/1922 | Smith .............. | A61C 9/0006 433/46 |

(Continued)

FOREIGN PATENT DOCUMENTS

KR        102106820 B1 *  5/2020  ............. A61C 17/10

*Primary Examiner* — Heidi M Eide
(74) *Attorney, Agent, or Firm* — The PL Law Group, PLLC

(57) ABSTRACT

A dental stent according to an embodiment includes handles and clamps which are decouplably coupled to main stent bodies depending on a purpose of use, the handles and the clamps enabling dental treatment and surgery to be performed safely and accurately. The dental stent is configured to include main stent bodies that are located in a maxillary or mandibular arch except for a treatment-target and surgical site in the same maxillary and mandibular arch and have respective square connection notches which enable respective handles or clamps to be decouplably coupled to the main stent bodies selectively depending on a purpose; an elastic clip that is coupled to upper ends of the main stent bodies and imparts elasticity to the main stent bodies; and light curing resins that are formed on respective inner walls of the main stent bodies and take a dental impression.

5 Claims, 9 Drawing Sheets

(56) References Cited

U.S. PATENT DOCUMENTS

| | | | | |
|---|---|---|---|---|
| 1,665,293 | A * | 4/1928 | Baratt | A61C 9/0006 |
| | | | | 433/47 |
| 2,611,959 | A * | 9/1952 | Baum | A61K 6/887 |
| | | | | 433/47 |
| 2,622,324 | A * | 12/1952 | Stone | A61C 9/0006 |
| | | | | 433/47 |
| 2011/0171593 | A1 * | 7/2011 | Ross | A61C 9/0006 |
| | | | | 433/41 |
| 2016/0310233 | A1 * | 10/2016 | Grande | A61C 1/084 |
| 2019/0298489 | A1 * | 10/2019 | Dingeldein | A61C 13/0001 |
| 2020/0205938 | A1 * | 7/2020 | Lee | A61B 6/5247 |
| 2021/0000570 | A1 * | 1/2021 | Chan | A61C 3/10 |

* cited by examiner

DENTAL STENT

CROSS REFERENCE TO RELATED APPLICATION AND CLAIM OF PRIORITY

This application claims the benefit under 35 USC § 119 of Korean Patent Application No. 10-2022-0065370, filed on May 27, 2022, in the Korean Intellectual Property Office, the entire disclosure of which is incorporated herein by reference for all purposes.

BACKGROUND

1. Field of the Invention

The present invention relates to a dental stent, and more specifically, to a dental stent including handles and clamps which are used by being decouplably coupled to main stent bodies depending on a purpose of use, the handles and the clamps enabling dental treatment and surgery to be performed safely and accurately.

2. Description of the Related Art

An implant procedure for replacing a tooth includes a process of making a gum incision to expose an alveolar bone and then forming a hole in the alveolar bone into which a fixture is implanted using a drill. A stent may be used as an assistant tool to guide a placement direction of the fixture and a location of the hole that is formed in the alveolar bone by a surgeon during drilling work of forming the hole.

The stent includes a guide hole 1a into which a drill is inserted when the hole is formed in the alveolar bone, a stent guide 1b which guides a location of the drill, and a stent support 1c which supports the stent guide. The stent support can be formed to cover all of the teeth or can be partially formed to cover only adjacent teeth and adjacent gingival surfaces located close to surgery target teeth depending on the number and the location of implant procedure target teeth.

The stent is designed by a software program and is output through a 3D printer or the like to be produced as an actual product based on a design result. According to the related art, a stent guide is designed to have a set height regardless of a length of the fixture, that is, a depth of drilling, and the depth of drilling is determined as a length of a drill used in the procedure.

According to the related art described above, it is inevitable to use drills having various lengths in accordance with the lengths of fixtures. Hence, there is an increase in the number of drills included in a surgical kit used in an implant procedure, which results in inconvenience of using several drills simultaneously depending on types of fixtures which are implanted in the procedure. The increase in the number of drills not only results in inconvenience to a surgeon and a patient but also becomes a factor that increases a purchase cost of the surgical kit and induces a difficulty in management thereof.

SUMMARY

An aspect of the invention is to provide a dental stent including handles and clamps which are used by being decouplably coupled to main stent bodies depending on a purpose of use, the handles and the clamps enabling dental treatment and surgery to be performed safely and accurately. Another aspect of the invention is to provide a dental stent having a light curing resin which is used for taking a dental impression, the light curing resin having a surface film which enables the light curing resin to be hygienically used by inhibiting excessive intrusion into an undercut side of a tooth and inhibiting foreign matter from penetrating the light curing resin from outside.

According to the invention, there is provided, as a means to achieve the above-described aspects, a dental stent technically configured to include: main stent bodies that are located in a maxillary or mandibular arch except for a treatment-target and surgical site in the same maxillary and mandibular arch and have respective square connection notches which enable respective handles or clamps to be decouplably coupled to the main stent bodies selectively depending on a purpose; an elastic clip that is coupled to upper ends of the main stent bodies and imparts elasticity to the main stent bodies; and light curing resins that are formed on respective inner walls of the main stent bodies and take a dental impression.

The elastic clip may have an inverted "U"-shaped body and may have lower end portions formed to be inclined inward such that the main stent bodies are smoothly inclined inward when the lower end portions of the elastic clip are forced to be inserted into and coupled to respective fitting holes formed at upper ends of the main stent bodies.

The light curing resins may have respective surface films formed on surfaces of the light curing resins, the surface film inhibiting excessive intrusion of the light curing resins filled inside into an undercut between teeth.

The handles that are decouplably coupled to the main stent bodies may have respective connection portions at lower ends which are decouplably coupled to the square connection notches, and a force applied to the handles after coupling may cause the main stent bodies to overcome an elastic force of the elastic clip and be separated from each other toward right and left sides, respectively.

The clamps that are decouplably coupled to the main stent bodies may have a fastening member screw-coupled to upper parts of the clamps and may be tightly screwed by the fastening member to inhibit the main stent bodies from moving, and the clamps may have respective close-contact portions which are formed at lower parts and come into close contact with the square connection notches, respectively.

A camera may be provided at a body of one of the clamps.

DETAILED DESCRIPTION

Hereinafter, embodiments of the invention will be described in detail with reference to the accompanying drawings. However, the invention is not limited to the embodiments described here and can be realized as various other embodiments. In addition, a part unrelated to the description is omitted from the drawings in order to clearly describe the invention.

In the entire specification, when a certain part "comprises" a certain configurational element, this doesn't mean that another configurational element is excluded but means that another configurational element can be further included unless specifically described otherwise.

Figure 1:
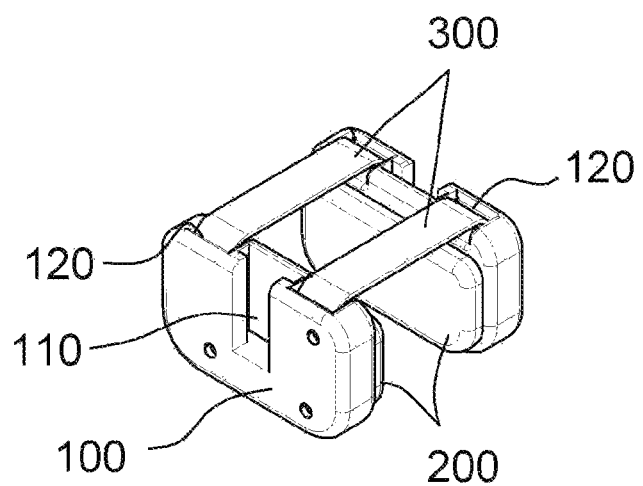
FIG. 1 is a perspective view of a dental stent according to the invention.
Figure 2:
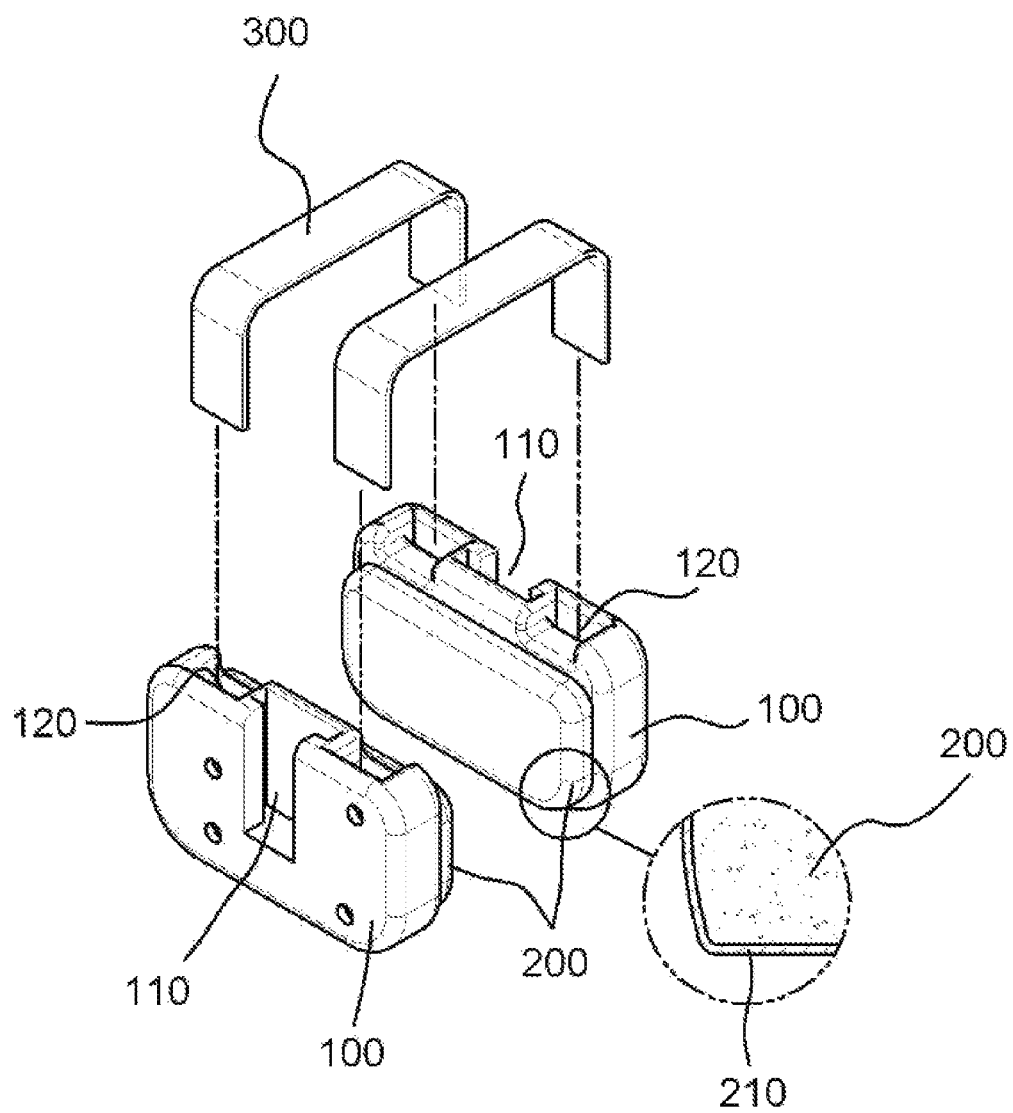
FIG. 2 is an exploded perspective view of the stent according to the invention.
Figure 3:
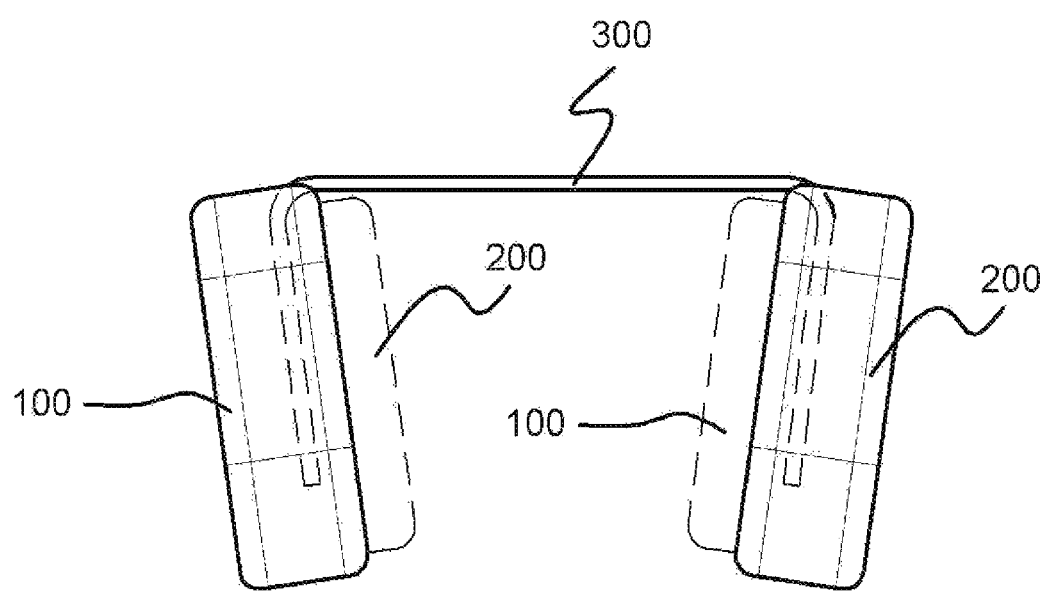
FIG. 3 is a front view illustrating a coupling state of the stent according to the invention.
Figure 4:
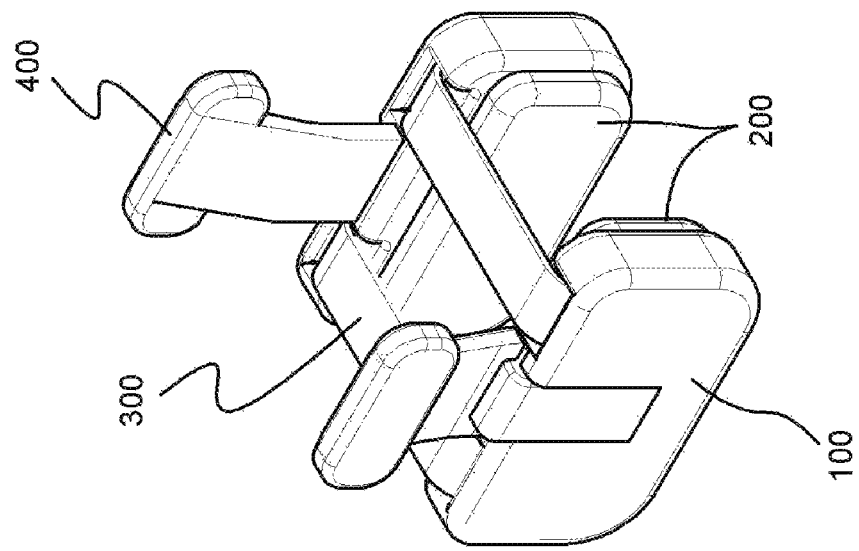
FIG. 4 is a perspective view illustrating a state in which handles are coupled to the stent according to the invention.
Figure 4:
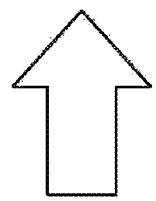
Figure 4:
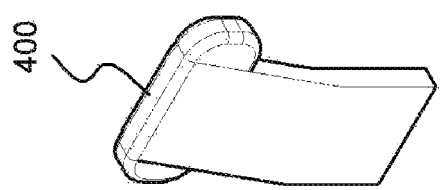
Figure 4:
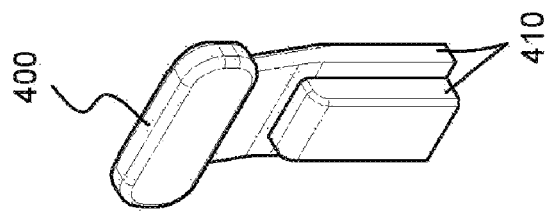
Figure 5:
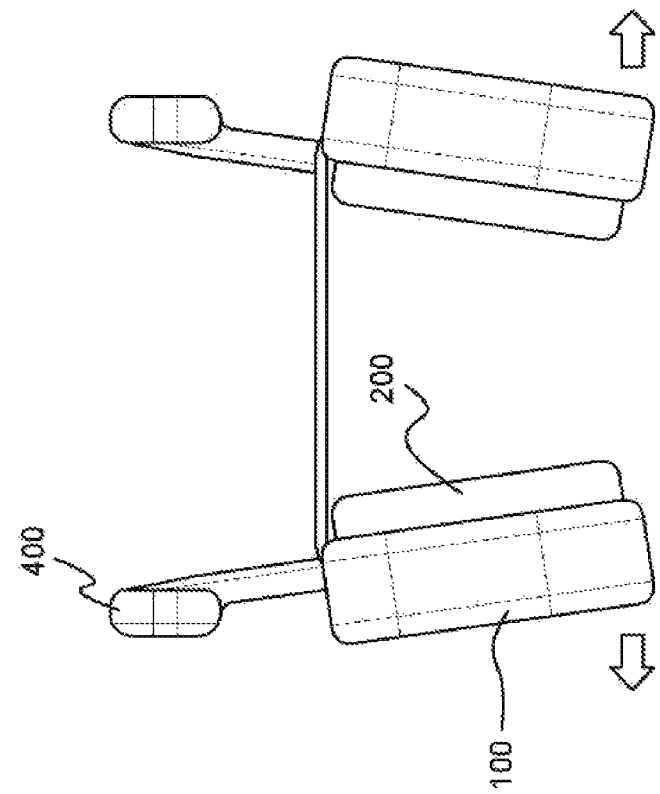
FIG. 5 is a front view illustrating a state in which the stent is separated by the handles according to the invention.
Figure 5:
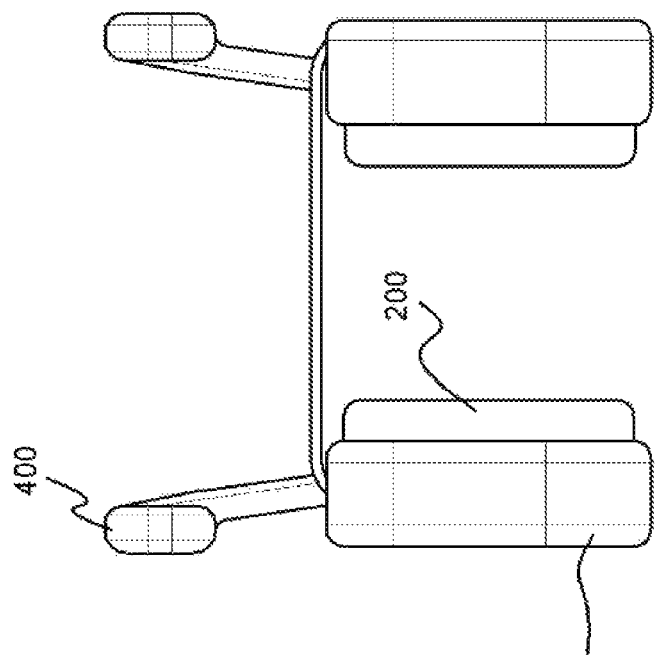
Figure 6:
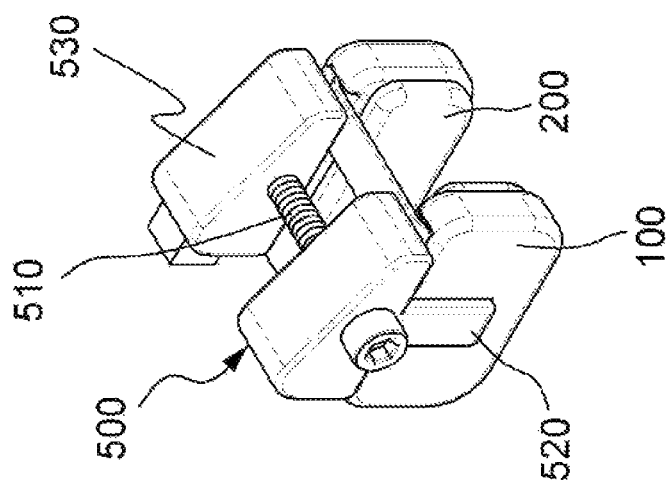
FIG. 6 is a front view illustrating a coupling state of clamps according to the invention.
Figure 7:
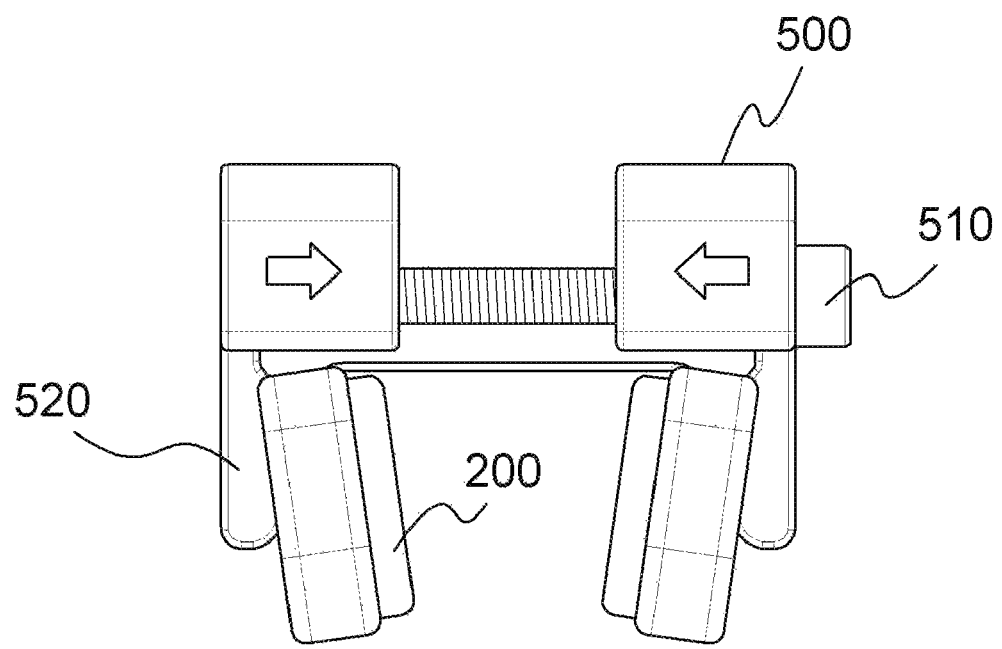
FIG. 7 is a front view illustrating a state in which the clamps are fastened to main stent bodies according to the invention.
Figure 8:
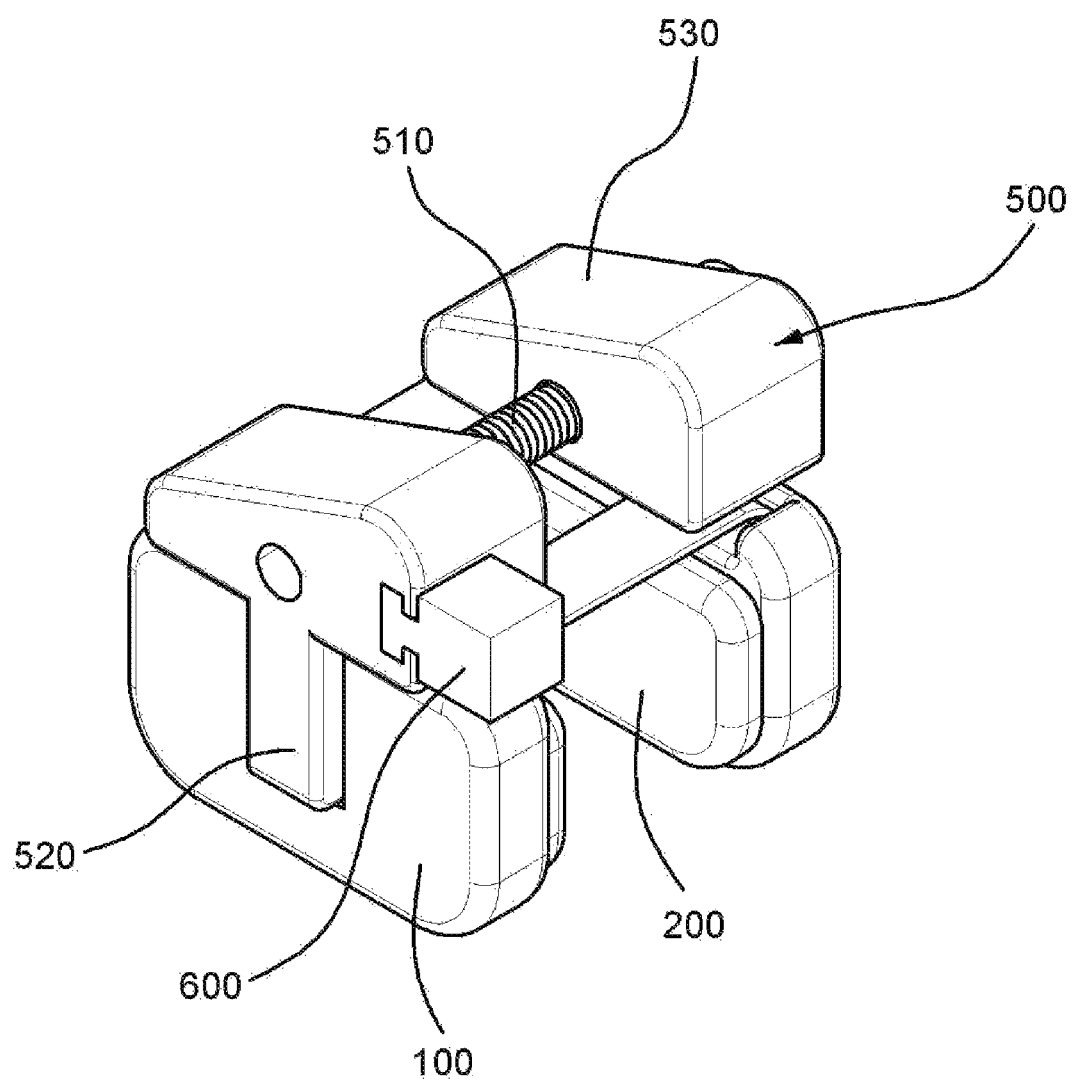
FIG. 8 is a perspective view illustrating a state in which a camera is attached to one clamp according to the invention.
Figure 9:
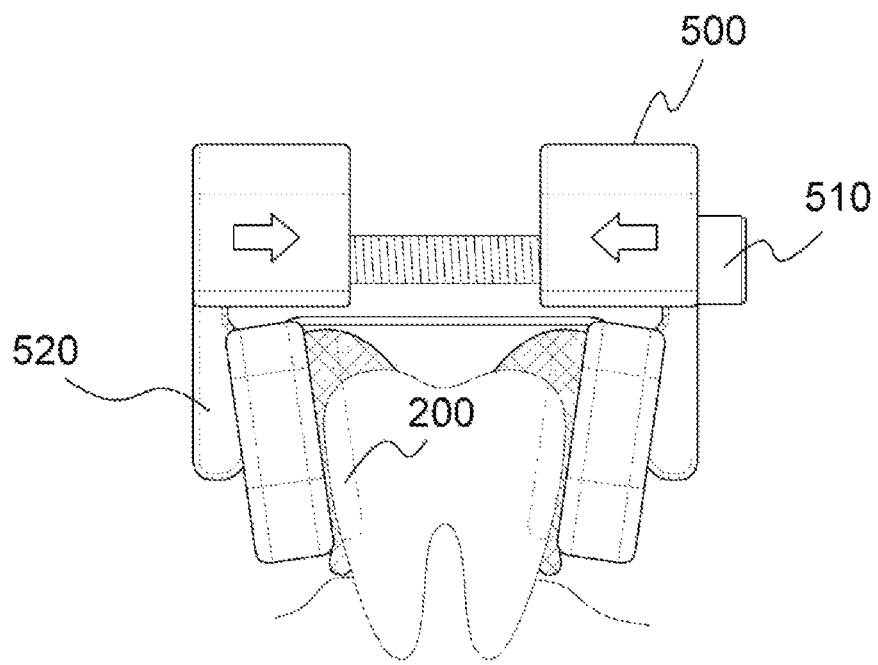
FIG. 9 is a front view illustrating a state of taking a dental impression by using a light curing resin according to the invention.

FIG. 1 is a perspective view of a dental stent according to the invention, FIG. 2 is an exploded perspective view of the stent according to the invention, FIG. 3 is a front view illustrating a coupling state of the stent according to the invention, FIG. 4 is a perspective view illustrating a state in which handles are coupled to the stent according to the invention, FIG. 5 is a front view illustrating a state in which the stent is separated by the handles according to the invention, FIG. 6 is a front view illustrating a coupling state of clamps according to the invention, FIG. 7 is a front view illustrating a state in which the clamps are fastened to main stent bodies according to the invention, FIG. 8 is a perspective view illustrating a state in which a camera is attached to one clamp according to the invention, and FIG. 9 is a front view illustrating a state of taking a dental impression by using a light curing resin according to the invention.

According to an example of the invention, there is provided a patient-specific stent in kit form.

With reference to FIGS. 1 to 7, the invention is a dental stent, and the stent includes main stent bodies 100, an elastic clip 300, and light curing resins 200. In addition, handles 400 and clamps 500 which are used by being decouplably coupled to the main stent bodies 100 depending on a purpose of use are used.

The main stent bodies 100 are located in a maxillary or mandibular arch except for a treatment-target or surgical site in the same maxillary and mandibular arch and have respective square connection notches 110 which enable the respective handles 400 or clamps 500 to be decouplably coupled to the main stent bodies selectively depending on a purpose. In addition, the main stent bodies 100 have respective fitting holes 120 into which the elastic clip 300 is inserted to be coupled to upper ends of the stent bodies. As illustrated in FIGS. 1 and 2, the stent is configured to have two identical main stent bodies 100, each of which has the square connection notch 110 and a fitting hole 120, and a pair of two parts having the same configuration is connected to each other through the elastic clip 300 to be used.

As illustrated in FIG. 3, the elastic clip 300 is coupled to upper ends of the main stent bodies 100 to fulfill a function of imparting elasticity to the main stent bodies 100. In this respect, the elastic clip 300 has an inverted "U"-shaped body and has both lower end portions formed to be inclined inward such that the main stent bodies 100 are smoothly inclined inward when the lower end portions of the elastic clip 300 are forced to be inserted into and coupled to the fitting holes 120 formed at upper ends of the main stent bodies 100.

A configuration of the main stent bodies which are inclined inward causes the handles 400 to have a forceps-like shape when the handles are coupled to the main stent bodies 100 such that clenching and opening movements of the main stent bodies 100 can be easily performed at a teeth side.

The light curing resins 200 are formed on respective inner walls of the main stent bodies 100 and fulfills a function of taking a dental impression.

The light curing resin 200 has a surface film 210 formed on the surface of the light curing resin, and the surface film 210 inhibits intrusion of the light curing resin 200 between teeth during taking a dental impression. After the dental impression is taken, an impression-taken area of the light curing resin 200 is cured by a light curing device (not illustrated). The surface film 210 has a thin film shape, an inside of the surface film 210 is filled with the light curing resin 200, and the surface film not only hygienically protects the filled light curing resin 200 from the outside but also inhibits excessive intrusion of the light curing resin 200 into an undercut between teeth.

The handles 400 and the clamps 500 which are decouplably coupled to the main stent bodies 100 have respective different functions. When the handles 400 or the clamps 500 are coupled to the main stent bodies 100, the stent is completely configured and is used as a kit. A sealed kit product contains the handles 400, the clamps 500, and completely assembled main stent bodies 100 in a sealed wrapper and is sold on a market, and a merchandised kit product is opened to be used as a disposable stent for dental treatment.

The handles 400 that are decouplably coupled to the main stent bodies 100 have respective connection portions 410 at lower ends which are decouplably coupled to the square connection notches 110, and the coupled handles are configured to cause the main stent bodies 100 to overcome an elastic force of the elastic clip 300 and be separated from each other toward right and left sides, respectively. When the handles 400 are coupled to the main stent bodies 100, a forceps-like structure is formed as illustrated in FIG. 5. In other words, the main stent bodies 100 are inclined inward due to the elastic clip 300, and the handles 400 are separated outward from each other.

In a state described above, when the handles 400 are pressed inward, the main stent bodies 100 overcome the elasticity of the elastic clip 300 and come into a state in which the main stent bodies are separated from each other toward the right and left sides. In this state, when the handles 400 are released after the stent is located in a maxillary or mandibular arch (generally, opposite natural tooth, anchor pin, abutment, crown, dentures, gum, or the like) except for a treatment-target and surgical site in the same maxillary and mandibular arch, the elasticity of the elastic clip 300 causes the main stent bodies 100 to come into a clenching state on the teeth side. In this state, the dental impression is taken by the light curing resin 200. After the dental impression is taken, the light curing resin 200 is cured by a light curing device.

The clamps 500 that are decouplably coupled to the main stent bodies 100 have a fastening member 510 screw-coupled to upper parts of the clamps and are tightly screwed by the fastening member to inhibit the main stent bodies 100 from moving, and the clamps have respective close-contact portions 520 which are formed at lower parts and come into close contact with the square connection notches 110, respectively.

The clamp 500 has an inclined surface 530 at one side of an upper end, and the inclined surface 530 causes an oral cavity to be smoothly opened. In addition, an inner surface of the close-contact portion 520 has a rounding shape such that tight screwing can be smoothly performed by the rounding-shaped close-contact portion 520 when the close-contact portion 520 comes into close contact with the square connection notch 110.

A main purpose of the clamps 500 configured as described above is to inhibit the separated main stent bodies 100 from moving or falling out to have an increase in angle thereof. In this respect, when the dental impression is taken, the handles 400 are decoupled from the main stent bodies 100, the close-contact portions 520 of the clamps 500 are located at the sides of the square connection notches 110 as illustrated in FIG. 7, and then the fastening member 510 is fastened so that the movement of the main stent bodies 100 is inhibited and a fixing force is increased. The clamps 500 configured as described above are used during dental treatment and surgery.

Meanwhile, it is also noted that a configuration in which a camera 600 is provided at the clamp 500 side as illustrated in FIG. 8 and the camera can image the inside of the oral cavity of a patient during the treatment and surgery in real time can be realized.

As described above, the description provided above focuses on the embodiments; however, the embodiments are described only as examples, and the invention is not limited thereto. In addition, it is possible for those of ordinary skill in the art to which the invention pertains to find that various modifications and applications of the invention which are not exemplified in the description provided above can be obtained within the scope not departing from essential characteristics of the embodiments. For example, each configurational element which is specifically described in the embodiments can be modified to be realized. Further, differences related to such modifications and applications are to be construed to be included in the scope of the invention which is specified in the accompanying claims.

As described above, according to the invention, there are prepared handles and clamps which are used by being decouplably coupled to main stent bodies depending on a purpose of use. Hence, the handles and the clamps enable dental treatment and surgery to be safely and accurately performed.

In addition, the invention is advantageous in that, since a light curing resin is used for taking a dental impression and has a surface film which not only inhibits a phenomenon of excessive intrusion of the light curing resin into an undercut between teeth, but also inhibits foreign matter from penetrating the light curing resin from outside, a dental impression can be hygienically taken.

While the present invention has been described with respect to the specific embodiments, it will be apparent to those skilled in the art that various changes and modifications may be made without departing from the spirit and scope of the invention as defined in the following claims.

What is claimed is:

1. A dental stent comprising:
   handles and clamps;
   main stent bodies that are to be located in an oral cavity, the main stent bodies having square connection notches through which the handles and/or the claimed clamps are capable of being coupled to the main stent bodies, in a detachable manner;
   an elastic clip that is coupled to the main stent bodies and imparts elasticity to the main stent bodies; and
   light curing resins that are formed on respective inner walls of the main stent bodies and take a dental impression,
   wherein the elastic clip has an inverted U-shaped body, in which legs of the inverted U-shaped body are formed to be inclined inward such that the main stent bodies are smoothly inclined inward when the lower end portions of the elastic clip are forced to be inserted into and coupled to respective fitting holes formed at upper ends of the main stent bodies.

2. The dental stent according to claim 1, wherein the light curing resins have respective surface films formed on surfaces of the light curing resins, the surface film inhibiting excessive intrusion of the light curing resins filled inside into an undercut between teeth.

3. The dental stent according to claim 1, wherein the clamps that are decouplably coupled to the main stent bodies have a fastening member screw-coupled to upper parts of the clamps and are tightly screwed by the fastening member to inhibit the main stent bodies from moving; and
   the clamps have respective close-contact portions which are formed at lower parts and come into close contact with the square connection notches, respectively.

4. The dental stent according to claim 3, wherein a camera is provided at a body of one of the clamps.

5. A dental stent comprising:
   handles and clamps;
   main stent bodies that are to be located in an oral cavity, the main stent bodies having square connection notches through which the handles and/or the claimed clamps are capable of being coupled to the main stent bodies, in a detachable manner;
   an elastic clip that is coupled to the main stent bodies and imparts elasticity to the main stent bodies; and
   light curing resins that are formed on respective inner walls of the main stent bodies and take a dental impression,
   wherein the handles that are decouplably coupled to the main stent bodies have respective connection portions at lower ends which are decouplably coupled to the square connection notches; and
   when the handles are coupled to the main stent bodies, a force applied to the handles causes the main stent bodies to overcome an elastic force of the elastic clip to cause separation of the main stent bodies relative to each other.

* * * * *